United States Patent
Medlock et al.

(10) Patent No.: US 9,981,935 B2
(45) Date of Patent: May 29, 2018

(54) FORMATION OF CHIRAL 4-CHROMANONES USING CHIRAL PYRROLIDINES IN THE PRESENCE OF ACIDS

(71) Applicant: DSM IP ASSETS B.V., Heerlen (NL)

(72) Inventors: Jonathan Alan Medlock, Basel (CH); Ulla Letinois, Basel (CH); Thomas Netscher, Basel (CH); Werner Bonrath, Basel (CH)

(73) Assignee: DSM IP ASSETS B.V., Heerlen (NL)

( * ) Notice: Subject to any disclaimer, the term of this patent is extended or adjusted under 35 U.S.C. 154(b) by 24 days.

(21) Appl. No.: 14/902,661

(22) PCT Filed: Jul. 3, 2014

(86) PCT No.: PCT/EP2014/064201
§ 371 (c)(1),
(2) Date: Jan. 4, 2016

(87) PCT Pub. No.: WO2015/001027
PCT Pub. Date: Jan. 8, 2015

(65) Prior Publication Data
US 2016/0168110 A1    Jun. 16, 2016

(30) Foreign Application Priority Data
Jul. 5, 2013  (EP) .................................. 13175334

(51) Int. Cl.
*C07D 311/02* (2006.01)
*C07D 311/22* (2006.01)

(52) U.S. Cl.
CPC ........ *C07D 311/22* (2013.01); *C07B 2200/09* (2013.01)

(58) Field of Classification Search
CPC ................................................... C07D 311/02
See application file for complete search history.

(56) References Cited

U.S. PATENT DOCUMENTS 4,415,741 A    11/1983  Kabbe

FOREIGN PATENT DOCUMENTS

EP    2 522 647    11/2012

OTHER PUBLICATIONS

IUPAC Gold Book. "Bronsted acid." © 2017. Available from: < http://goldbook.iupac.org/html/B/B00744.html >.*
Chapelet, J. "Asymmetric synthesis of 2,2-disubstituted chromanols—Novel approaches to Vitamin E analogues." (2009), University of Basel, Basel, Switzerland. Available from: < http://edoc.unibas.ch/1038/1/THESIS_-_J._CHAPELAT_-_2009.pdf >.*
Kabbe et al., "Synthesen and Umsetzungen von 4-Chromanonen", *Angewandte Chemie*, vol. 94, Jan. 1, 1982, pp. 254-262.
Pearce et al., "Inhibitors of Cholesterol Biosynthesis. 2. Hypochlesterolemic and Antioxidant Activities of Benzopyran and Tetrahydronaphthalene Analogues of the Tocotrienols.Opyran and Tetrahydronphthalene", *Journal of Medicinal Chemistry*, American Chemical Society, vol. 37, No. 4, Feb. 18, 1994, pp. 526-541.
Rios et al., "Highly enantioselective synthesis of 2H-1-benzothiopyrans by a catalytic domino reaction", *Tetrahedron Letters*, vol. 47, No. 48, Nov. 27, 2006, pp. 8547-8551.
Nunez et al., "Asymmetric organocatalytic synthesis of six-membered oxygenated heterocycles", *Tetrahedron*, vol. 66, No. 12, Mar. 20, 2010, pp. 2089-2109.
Wang et al., "Enantio- and diastereoselective Michael addition reactions of unmodified aldehydes and ketones with nitroolefins catalyzed by a pyrroldine sulfonamide", *Chem. Eur. J.*, vol. 2006, No. 12, 2006, pp. 4321-4332.
International Search Report for PCT/EP2014/064201 dated Sep. 29, 2014, four pages.
Written Opinion of the ISA for PCT/EP2014/064201 dated Sep. 29, 2014, four pages.

* cited by examiner

*Primary Examiner* — Noble E Jarrell
*Assistant Examiner* — John S Kenyon
(74) *Attorney, Agent, or Firm* — Nixon & Vanderhye P.C.

(57) ABSTRACT

The present invention relates to a synthesis of chromanones or chromanes in a stereospecific matter in view of the 2-position in the chromanone or chromane ring. It has been found that this synthesis is particularly possible in the presence of a chiral compound of a specific type and of at least one Bransted acid or in the presence a specific chiral compound having a Bransted acid functional group in the molecule.

12 Claims, No Drawings

FORMATION OF CHIRAL 4-CHROMANONES USING CHIRAL PYRROLIDINES IN THE PRESENCE OF ACIDS

This application is the U.S. national phase of International Application No. PCT/EP2014/064201 filed 3 Jul. 2014 which designated the U.S. and claims priority to EP Patent Application No. 13175334.5 filed 5 Jul. 2013, the entire contents of each of which are hereby incorporated by reference.

TECHNICAL FIELD

The present invention relates to the field of the synthesis of tocopherols and tocotrienols.

BACKGROUND OF THE INVENTION

Chromane compounds represent an important class of chiral natural products and bioactive compounds. An important class of chromane compounds are vitamin E and its esters. Often vitamin E is commercialized in the form of its esters because the latter show an enhanced stability.

On the one hand the typical technical synthesis of vitamin E leads to mixtures of isomers. On the other hand higher bioactivity (biopotency) has been shown to occur in general by tocopherols and tocotrienols having the R-configuration at the chiral centre situated next to the ether atom in the ring of the molecule (indicated by * in the formulas used later on in the present document) (i.e. 2R-configuration), as compared to the corresponding isomers having S-configuration. Particularly active are the isomers of tocopherols having the natural configuration at all chiral centres, for example (R,R,R)-tocopherols, as has been disclosed for example by H. Weiser et al. in *J. Nutr.* 1996, 126 (10), 2539-49. This leads to a strong desire for an efficient process for separating the isomers. Hence, the isomer separation not only of vitamin E, but also of their esters, particularly their acetates, as well as of their precursors is of prime interest.

Separation of all the isomers by chromatographic methods is extremely difficult and costly.

To overcome these inherent problems, it has been tried to offer stereospecific synthesis allowing the preferential formation of the desired isomers only. However, these methods are very expensive, complex and/or exotic as compared to the traditional industrial synthesis leading to isomer mixtures.

Therefore, there exists a large interest in providing stereospecific synthesis routes leading to the desired isomer. Particular difficult is to achieve specifically the desired chirality at the chiral carbon centre in the 2-position of the chromane ring.

A synthetic pathway for chromanes is via their corresponding chromanones. It is known from Kabbe and Heitzer, *Synthesis* 1978; (12): 888-889 that α-tocopherol can be synthesized via α-tocotrienol from 4-oxo-α-tocotrienol which is accessible from 2-acetyl-3,5,6-trimethylhydroquinone and farnesylacetone in the presence of pyrrolidine. However, this procedure leads to a racemic mixture in view of the configuration at the 2-position of the chromane respectively chromanone ring.

SUMMARY OF THE INVENTION

Therefore, the problem to be solved by the present invention is to offer a method for the synthesis of chromanones or chromanes, i.e. of compounds of formula (I) or (V) in a stereospecific matter in view of the 2-position in the chromanone or chromane ring.

Surprisingly, it has been found that a process for the manufacturing according to claim 1 is able to solve this problem.

It has been particularly found that the combination of a specific chiral compound and a specific Brønsted acid or Brønsted acid group leads to the formation of the desired product and a desired stereoselective formation. Particularly, the desired isomer is formed in preference over the non-desired isomer yielding to an enantiomeric ratio being larger than zero or a ratio of [2R]-stereoisomers to [2S]-stereoisomers being larger than one.

Further aspects of the invention are subject of further independent claims. Particularly preferred embodiments are subject of dependent claims.

DETAILED DESCRIPTION OF THE INVENTION

In a first aspect the present invention relates to a process for the manufacturing of a compound of formula (I)

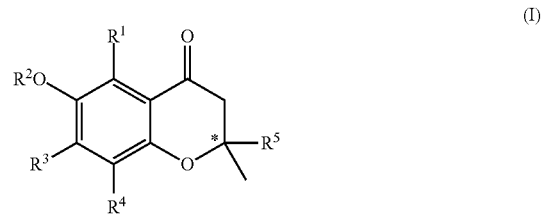

comprising the step of reacting a compound of formula (II-A) and a compound of formula (II-B) or a ketal thereof in the presence of an organic solvent and
either
of at least one chiral compound of formula (II-C) and of at least one Brønsted acid having a $pK_a$ of between 5 and 10.5, measured at 25° C. in DMSO;
or
of at least one chiral compound of formula (II-C-A) having a $pK_a$ of between 5 and 10.5, measured at 25° C. in DMSO, or an internal salt thereof

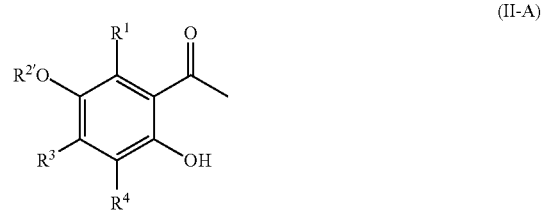

-continued

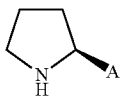
(II-C-A)

wherein $R^1$, $R^3$ and $R^4$ are independently from each other hydrogen or methyl groups;

$R^2$ and $R^{2'}$ represents hydrogen or a phenol protection group;

$R^5$ represents either a linear or branched completely saturated $C_{6-25}$-alkyl group or a linear or branched $C_{6-25}$-alkyl group comprising at least one carbon-carbon double bond;

$Y^1$ represents either $CH_2Y^2$ or

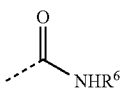

wherein $R^6$ represents a linear or branched $C_{1-12}$-alkyl group which optionally further comprises at least one aromatic group and/or C=O and/or NH and/or $NH_2$ group;

$Y^2$ represents either OH or $OR^7$ or $NHR^7$ or $NHCOOR^7$ or

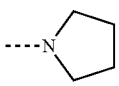

wherein $R^7$ represents either
  a linear or branched $C_{1-12}$-alkyl group which optionally further comprises at least one aromatic group and/or C=O and/or NH and/or $NH_2$ group
  or
  an aryl group or a substituted aryl group or a heteroaryl group or a substituted heteroaryl group and A represents a substituent carrying a Brønsted acid functional group and the dotted line(s) represents the bond(s) by which the corresponding substituent is bound to the rest of formula (II-C);

and wherein * represents the chiral centre of the chiral isomer of formula (I).

The term "independently from each other" in this document means, in the context of substituents, moieties, or groups, that identically designated substituents, moieties, or groups can occur simultaneously with a different meaning in the same molecule.

A "$C_{x-y}$-alkyl", resp. "$C_{x-y}$-acyl" group, is an alkyl resp. an acyl group comprising x to y carbon atoms, i.e. for example an $C_{1-3}$-alkyl group, is an alkyl group comprising 1 to 3 carbon atoms. The alkyl resp. the acyl group can be linear or branched. For example —CH(CH$_3$)—CH$_2$—CH$_3$ is considered as a $C_4$-alkyl group.

A "$C_{x-y}$-alkylene" group is an alkylene group comprising x to y carbon atoms, i.e., for example $C_2$-$C_6$ alkylene group is an alkyl group comprising 2 to 6 carbon atoms. The alkylene group can be linear or branched. For example the group —CH(CH$_3$)—CH$_2$— is considered as a $C_3$-alkylene group.

The term "hydrogen" means in the present document H and not $H_2$.

The sign * in formulae of molecules represents in this document a chiral centre in said molecule.

In the present document any single dotted line represents the bond by which a substituent is bound to the rest of a molecule.

The chirality of an individual chiral carbon centre is indicated by the label R or S according to the rules defined by R. S. Cahn, C. K. Ingold and V. Prelog. This R/S-concept and rules for the determination of the absolute configuration in stereochemistry is known to the person skilled in the art.

The "$pK_a$" is commonly known as negative decadic logarithm of the acid dissociation constant ($pK_a=-\log_{10} K_a$). When the organic acid has several protons the $pK_a$ as used in this document relates to the dissociation constant of the first proton ($K_{a1}$). The $pK_a$ is measured at 25° C. in DMSO. The method of measuring the $pK_a$ at 25° C. in DMSO is described in detail in *J. Am. Chem. Soc.* 1975, 97, 7006-7014. All values of $pK_a$ given in this document are to be determined according to said method.

The residue $R^5$ represents either a linear or branched completely saturated $C_{6-25}$-alkyl group or a linear or branched $C_{6-25}$-alkyl group comprising at least one carbon-carbon double bond.

Preferably the group $R^5$ is of formula (III).

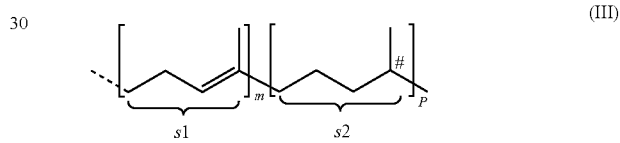
(III)

In formula (III) m and p stand independently from each other for a value of 0 to 5 provided that the sum of m and p is 1 to 5. Furthermore, the substructures in formula (III) represented by s1 and s2 can be in any sequence. The dotted line represents the bond by which the substituent of formula (III) is bound to the rest of the compound of formula (II-B) or formula (I). Furthermore, # represents a chiral centre, obviously except in case where said centre is linked to two methyl groups.

It is preferred that group $R^5$ is of formula (III-x).

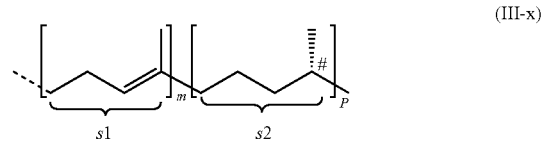
(III-x)

As mentioned above the substructures in formula (III) represented by s1 and s2 can be in any sequence. It is, therefore, obvious that in case that the terminal group is having the substructure s2, this terminal substructure has no chiral centre.

In one preferred embodiment m stands for 3 and p for 0.

In another preferred embodiment p stands for 3 and m for 0.

Therefore, $R^5$ is preferably of formula (III-A), particularly (III-ARR), or (III-B).

(III-A)

(III-APR)

(III-B)

Preferred are the following combinations of $R^1$, $R^3$ and $R^4$:

$R^1=R^3=R^4=CH_3$ or $R^1=R^4=CH_3$, $R^3=H$ or $R^1=H$, $R^3=R^4=CH_3$ or $R^1=R^3=H$, $R^4=CH_3$ $R^2$ and $R^{2'}$ represents either hydrogen or a phenol protection group.

A phenol protection group is a group which protects the phenolic group (OH in formula (I) or (II-A)) and can be deprotected easily, i.e. by state-of-the-art methods, to the phenolic group again.

The phenol protection group forms with the rest of the molecule a chemical functionality which is particularly selected from the group consisting of ester, ether or acetal. The protection group can be easily removed by standard methods known to the person skilled in the art.

In case where the phenol protection group forms with the rest of the molecule an ether, the substituent $R^2$ or $R^{2'}$ is particularly a linear or branched $C_{1-10}$-alkyl or cycloalkyl or aralkyl group. Preferably the substituent $R^2$ or $R^{2'}$ is a benzyl group or a substituted benzyl group, particularly preferred a benzyl group.

In case where the phenol protection group forms with the rest of the molecule an ester, the ester is an ester of an organic or inorganic acid.

If the ester is an ester of an organic acid, the organic acid can be a monocarboxylic acid or a polycarboxylic acid, i.e. an acid having two or more COOH-groups. Polycarboxylic acids are preferably malonic acid, succinic acid, glutaric acid, adipic acid, maleic acid or fumaric acid.

Preferably the organic acid is a monocarboxylic acid.

Hence, the substituent $R^2$ or $R^{2'}$ is preferably an acyl group. The acyl group is particularly a $C_{1-7}$-acyl, preferably acetyl, trifluoroacetyl, propionyl or benzoyl group, or a substituted benzoyl group.

If the ester is an ester of an inorganic acid, the inorganic acid is preferably nitric acid or a polyprotic acid, i.e. an acid able to donate more than one proton per acid molecule, particularly selected from the group consisting of phosphoric acid, pyrophosphoric acid, phosphorous acid, sulphuric acid and sulphurous acid.

In case where the phenol protection group forms with the rest of the molecule an acetal, the substituent $R^2$ or $R^{2'}$ is preferably with n=0 or 1.

Hence, the acetals formed so are preferably methoxymethyl ether (MOM-ether), β-methoxyethoxymethyl ether (MEM-ether) or tetrahydropyranyl ether (THP-ether). The protection group can easily be removed by acid.

The protecting group is introduced by reaction of the corresponding molecule having an $R^2$ resp. $R^{2'}$ being H with a protecting agent.

The protecting agents leading to the corresponding phenol protection groups are known to the person skilled in the art, as well as the chemical process and conditions for this reaction. If, for example, the phenol protection group forms with the rest of the molecule an ester, the suitable protecting agent is for example an acid, an anhydride or an acyl halide.

In the case that an ester is formed by the above reaction with the protecting agent, and that said ester is an ester of an organic polycarboxylic acid or an inorganic polyprotic acid, not necessarily all acid groups are esterified to qualify as protected in the sense of this document. Preferable esters of inorganic polyprotic acids are phosphates.

It is preferred that the protection group $R^2$ resp. $R^{2'}$ is a benzoyl group or a $C_{1-4}$-acyl group, particularly acetyl or trifluoroacetyl group. The molecules in which $R^2$ resp. $R^{2'}$ represents an acyl group, particularly an acetyl group, can be easily prepared from the corresponding unprotected molecule by esterification, respectively the phenolic compound can be obtained from the corresponding ester by ester hydrolysis.

It is important to realize that the step of reacting with the protecting agent can occur at different stages of manufacture of compound of formula (I) or of formula (V), the preparation of which is described later in this document in more detail, i.e. the reaction can occur for example at the level of compound of formula (II-A) or before or after preparation of compound (I) or compound (V).

It is particularly preferred that $R^2$ and $R^{2'}$ is H.

The process of the present invention comprises the steps of reacting compound of formula (II-A) and compound of formula (II-B) or a ketal thereof.

The corresponding compounds of (II-A) and compound of formula (II-B) or a ketal thereof are easily accessible. For example compounds of (II-A) can be synthesized from the method disclosed in G. Manecke, G. Bourwieg, *Chem. Ber.* 1962, 95, 1413-1416.

The mentioned reaction between compound of formula (II-A) and compound of formula (II-B) or a ketal thereof is done in the first embodiment in the presence of at least one chiral compound of formula (II-C) and of at least one Brønsted acid having a $pK_a$ of between 5 and 10.5, measured at 25° C. in DMSO.

(II-C)

The group $Y^1$ represents either $CH_2Y^2$ or

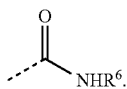

$R^6$ represents in first instance a linear or branched $C_{1-12}$-alkyl group. Particularly suitable linear or branched $C_{1-12}$-alkyl groups are methyl, ethyl, n-propyl, iso-propyl, n-butyl, iso-butyl, sec-butyl, tert-butyl, pentyl, hexyl, heptyl and octyl groups.

$R^6$ represents in second instance a linear or branched $C_{1-12}$-alkyl group which comprises further at least one aromatic group and/or C=O and/or NH and/or $NH_2$ group. Examples of suitable compounds of formula (II-C) for this embodiment are

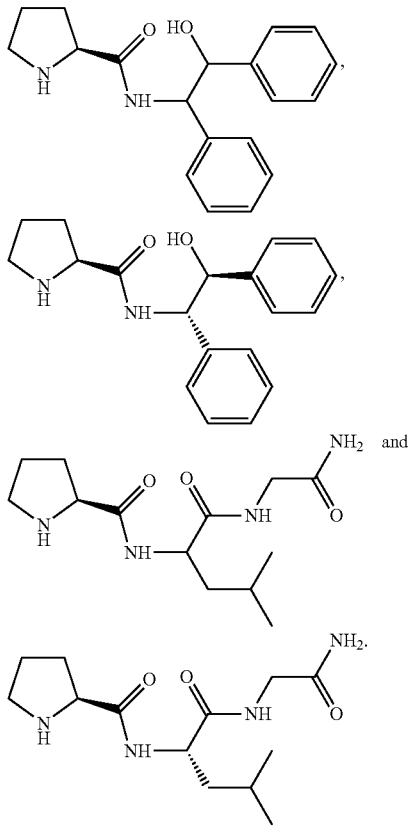

$Y^2$ represents either OH or $OR^7$ or $NHR^7$ or $NHCOOR^7$ or

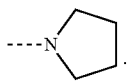

$R^7$ represents in a first instance a linear or branched $C_{1-12}$-alkyl group. Particularly suitable linear or branched $C_{1-12}$-alkyl groups are methyl, ethyl, n-propyl, iso-propyl, n-butyl, iso-butyl, sec-butyl, tert-butyl, pentyl, hexyl, heptyl and octyl groups.

$R^7$ represents in a second instance a linear or branched $C_{1-12}$-alkyl group which further comprises at least one aromatic group and/or C=O and/or NH and/or $NH_2$ group.

$R^7$ represents in a third instance an aryl group or a substituted aryl group or a heteroaryl group or a substituted heteroaryl group. The aryl group or a substituted aryl group or a heteroaryl group or a substituted heteroaryl group is particularly

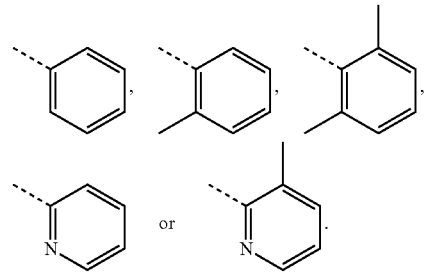

It is preferred that the compound of formula (II-C) is selected from the group consisting of

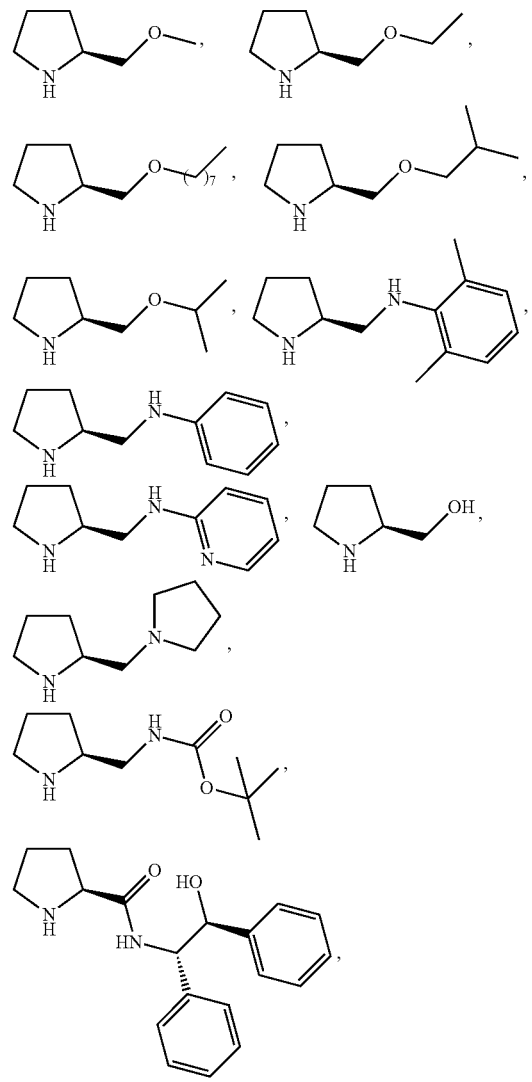

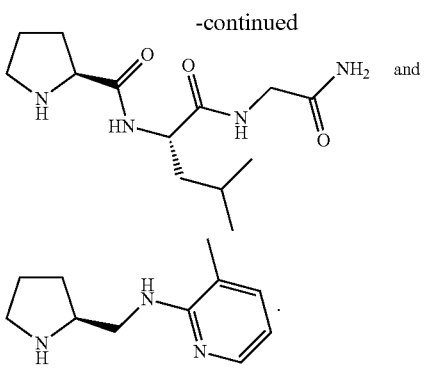

The compounds of formula (II-B) can be synthesized from corresponding precursors, for example the compound (E,E)-farnesylacetone from nerolidol by a chain-elongation reaction, as described in WO 2009/019132.

In one preferred embodiment the group $R^5$ does not comprise any chiral centres. The compound of formula (II-B) is preferred from the group consisting of (E)-6,10-dimethylundeca-5,9-dien-2-one, (5E,9E)-6,10,14-trimethylpentadeca-5,9,13-trien-2-one and (5E,9E,13E)-6,10,14,18-tetramethylnonadeca-5,9,13,17-tetraen-2-one, particularly (5E,9E)-6,10,14-trimethylpentadeca-5,9,13-trien-2-one.

When the group $R^5$ comprises chiral centres, it is preferred that the compound of formula (II-B) is in a form of pure chiral isomers.

This can be either achieved by stereospecific synthesis routes or by isolation of naturally occurring compounds or derived thereof or by separation from a mixture of the chiral stereoisomers.

For example (6R,10R)-6,10,14-trimethylpentadecan-2-one can be obtained from naturally occurring (R,R)-phytol by oxidation with $NaIO_4$ and a catalytic amount of $RuCl_3$ as disclosed by Thomas Eltz et al. in *J. Chem. Ecol.* (2010) 36:1322-1326.

In another preferred embodiment the compound of formula (II-B) is a methyl ketone having at least a carbon-carbon double bond in the γ,δ-position to the keto group. Preferably it is selected from the group consisting of 6-methylhept-5-en-2-one, (E)-6,10-dimethylundec-5-en-2-one, (Z)-6,10-dimethylundec-5-en-2-one, (E)-6,10-dimethylundeca-5,9-dien-2-one, (Z)-6,10-dimethylundeca-5,9-dien-2-one, (E)-6,10,14-trimethylpentadec-5-en-2-one, (Z)-6,10,14-trimethylpentadec-5-en-2-one; (5E,9E)-6,10,14-trimethylpentadeca-5,9-dien-2-one, (5E,9Z)-6,10,14-trimethylpentadeca-5,9-dien-2-one, (5Z,9E)-6,10,14-trimethylpentadeca-5,9-dien-2-one, (5Z,9Z)-6,10,14-trimethylpentadeca-5,9-dien-2-one; (E)-6,10,14-trimethylpentadeca-5,13-dien-2-one, (Z)-6,10,14-trimethylpentadeca-5,13-dien-2-one; (5E,9E)-6,10,14-trimethylpentadeca-5,9,13-trien-2-one, (5E,9Z)-6,10,14-trimethylpentadeca-5,9,13-trien-2-one, (5Z,9E)-6,10,14-trimethylpentadeca-5,9,13-trien-2-one, (5Z,9Z)-6,10,14-trimethylpentadeca-5,9,13-trien-2-one; (E)-6,10,14,18-tetramethylnonadec-5-en-2-one, (Z)-6,10,14,18-tetramethylnonadec-5-en-2-one; (5E,9E)-6,10,14,18-tetramethylnonadeca-5,9-dien-2-one, (5E,9Z)-6,10,14,18-tetramethylnonadeca-5,9-dien-2-one, (5Z,9E)-6,10,14,18-tetra-methylnonadeca-5,9-dien-2-one, (5Z,9Z)-6,10,14,18-tetramethylnonadeca-5,9-dien-2-one; (5E,13E)-6,10,14,18-tetramethylnonadeca-5,13-dien-2-one, (5E,13Z)-6,10,14,18-tetramethylnonadeca-5,13-dien-2-one, (5Z,13E)-6,10,14,18-tetra-methylnonadeca-5,13-dien-2-one, (5Z,13Z)-6,10,14,18-tetramethylnonadeca-5,13-dien-2-one; (E)-6,10,14,18-tetramethylnonadeca-5,17-dien-2-one, (Z)-6,10,14,18-tetramethylnonadeca-5,17-dien-2-one; (5E,9E,13E)-6,10,14,18-tetramethyl-nonadeca-5,9,13-trien-2-one, (5E,9E,13Z)-6,10,14,18-tetramethylnonadeca-5,9,13-trien-2-one, (5E,9Z,13E)-6,10,14,18-tetramethylnonadeca-5,9,13-trien-2-one, (5E,9Z,13Z)-6,10,14,18-tetramethylnonadeca-5,9,13-trien-2-one, (5Z,9E,13E)-6,10,14,18-tetramethylnonadeca-5,9,13-trien-2-one, (5Z,9E,13Z)-6,10,14,18-tetramethylnonadeca-5,9,13-trien-2-one, (5Z,9Z,13E)-6,10,14,18-tetra-methylnonadeca-5,9,13-trien-2-one, (5Z,9Z,13Z)-6,10,14,18-tetramethylnona-deca-5,9,13-trien-2-one; (5E,13E)-6,10,14,18-tetramethylnonadeca-5,13,17-trien-2-one, (5E,13Z)-6,10,14,18-tetramethylnonadeca-5,13,17-trien-2-one, (5Z,13E)-6,10,14,18-tetramethylnonadeca-5,13,17-trien-2-one, (5Z,13Z)-6,10,14,18-tetramethylnonadeca-5,13,17-trien-2-one; (5E,9E)-6,10,14,18-tetramethylnonadeca-5,9,17-trien-2-one, (5E,9Z)-6,10,14,18-tetramethylnonadeca-5,9,17-trien-2-one, (5Z,9E)-6,10,14,18-tetramethylnonadeca-5,9,17-trien-2-one, (5Z,9Z)-6,10,14,18-tetramethylnonadeca-5,9,17-trien-2-one; (5E,9E,13E)-6,10,14,18-tetramethyl-nonadeca-5,9,13,17-tetraen-2-one, (5E,9E,13Z)-6,10,14,18-tetramethylnonadeca-5,9,13,17-tetraen-2-one, (5E,9Z,13E)-6,10,14,18-tetramethylnonadeca-5,9,13,17-tetraen-2-one, (5E,9Z,13Z)-6,10,14,18-tetramethylnonadeca-5,9,13,17-tetraen-2-one, (ZE,9E,13E)-6,10,14,18-tetramethylnonadeca-5,9,13,17-tetraen-2-one, (5Z,9E,13Z)-6,10,14,18-tetramethylnonadeca-5,9,13,17-tetraen-2-one, (5Z,9Z,13E)-6,10,14,18-tetramethylnonadeca-5,9,13,17-tetraen-2-one, (5Z,9Z,13Z)-6,10,14,18-tetramethylnonadeca-5,9,13,17-tetraen-2-one, (5E,9E,13E)-6,10,14,18-tetramethylnonadeca-5,9,13-trien-2-one.

In case there are chiral centres in the group $R^5$, particularly if $R^5$ has the formula (III-ARR), the corresponding compounds of formula (II-B) can be prepared by asymmetrically hydrogenating olefinic unsaturated precursors thereof using chiral iridium complexes as disclosed in WO 2006/066863 A1 and WO 2012/152779 A1 the entire content of which is hereby incorporated by reference.

In case the compounds just mentioned have chiral carbon centre(s) it is preferred that said chiral centre(s) has/have the configuration as indicated in formula (III-x).

Preferably the compound of formula (II-B) in this embodiment is (E)-6,10-dimethylundec-5,9-dien-2-one (geranyl acetone) or (Z)-6,10-dimethylundec-5,9-dien-2-one (neryl acetone) or (5E,9E)-6,10,14-trimethylpentadeca-5,9-dien-2-one (E,E-farnesylacetone) or (5Z,9Z)-6,10,14-trimethylpentadeca-5,9-dien-2-one (Z,Z-farnesylacetone) or (E)-6,10-dimethylundec-5-en-2-one or (Z)-6,10-dimethylundec-5-en-2-one or (E)-6,10,14-trimethylpentadec-5-en-2-one or (Z)-6,10,14-trimethylpentadec-5-en-2-one, preferably geranyl acetone or E,E-farnesylacetone or (Z)-6,10-dimethylundec-5-en-2-one or (Z)-6,10,14-trimethylpentadec-5-en-2-one, more preferably geranyl acetone or E,E-farnesylacetone.

More preferred the compound of formula (II-B) is 6,10-dimethylundecan-2-one or 6,10,14-trimethylpentadecan-2-one.

Most preferred the compound of formula (II-B) is either (6R),10-dimethylundecan-2-one or (6R,10R),14-trimethylpentadecan-2-one.

In one embodiment a compound of formula (II-A) is reacted with a ketal of a compound, i.e. a ketone, of formula (II-B) in the presence either of at least one chiral compound of formula (II-C) and of at least one Brønsted acid having a pK$_a$ of between 5 and 10.5, measured at 25° C. in DMSO;

or of at least one chiral compound of formula (II-C-A) having a pK$_a$ of between 5 and 10.5, measured at 25° C. in DMSO, or an internal salt thereof.

The formation of a ketal from a ketone, per se, is known to the person skilled in the art.

The ketal of a ketone of formula (II-B) can be preferably formed from the ketone of formula (II-B) and an alcohol.

It is known to the person skilled in the art that there are alternative routes of synthesis for ketals. In principle, the ketal can also be formed by treating a ketone with orthoesters or by trans-ketalization such as disclosed for example in Pério et al., *Tetrahedron Letters* 1997, 38 (45), 7867-7870, or in Lorette and Howard, *J. Org. Chem.* 1960, 521-525, the entire content of both is hereby incorporated by reference.

Preferably the ketal is formed from the above mentioned ketone of formula (II-B) and an alcohol.

The alcohol can comprise one or more hydroxyl groups. The alcohol may be a phenolic alcohol or an aliphatic or cycloaliphatic alcohol. Preferably the alcohol has one or two hydroxyl groups.

In case the alcohol has one hydroxyl group, the alcohol is preferably an alcohol which has 1 to 12 carbon atoms. Particularly, the alcohol having one hydroxyl group is selected from the group consisting of methanol, ethanol, 1-propanol, 2-propanol, 1-butanol, 2-methyl-1-propanol, 2-butanol, pentane-1-ol, 3-methylbutane-1-ol, 2-methylbutane-1-ol, 2,2-dimethylpropan-1-ol, pentane-3-ol, pentane-2-ol, 3-methylbutane-2-ol, 2-methylbutan-2-ol, hexane-1-ol, hexane-2-ol, hexane-3-ol, 2-methyl-1-pentanol, 3-methyl-1-pentanol, 4-methyl-1-pentanol, 3-methyl-2-pentanol, 4-methyl-2-pentanol, 2-methyl-3-pentanol, 2,2-dimethyl-1-butanol, 2,3-dimethyl-1-butanol, 3,3-dimethyl-1-butanol, 3,3-dimethyl-2-butanol, 2-ethyl-1-butanol, and all structural isomers of heptanol, octanol and halogenated C$_{1-8}$-alkyl alcohols, particularly 2,2,2-trifluoroethanol. Particularly suitable are primary or secondary alcohols. Preferably primary alcohols are used as alcohols with one hydroxyl group.

In another embodiment the alcohol is a diol, hence has two hydroxyl groups. Preferably the diol is selected from the group consisting of ethane-1,2-diol, propane-1,2-diol, propane-1,3-diol, butane-1,4-diol, butane-1,3-diol, butane-1,2-diol, butane-2,3-diol, 2-methylpropane-1,2-diol, 2,2-dimethylpropane-1,3-diol, 1,2-dimethylpropane-1,3-diol, benzene-1,2-diol and cyclohexane-1,2-diols. From two cyclohexane-1,2-diols the preferred stereoisomer is syn-cyclohexane-1,2-diol (=cis-cyclohexane-1,2-diol).

The two hydroxyl group are in one embodiment bound to two adjacent carbon atoms, hence these diols are vicinal diols. Vicinal diols form a 5 membered ring in a ketal.

Particularly suitable are vicinal diols which are selected from the group consisting of ethane-1,2-diol, propane-1,2-diol, butane-1,2-diol, butane-2,3-diol, 2-methylpropane-1,2-diol, benzene-1,2-diol and syn-cyclohexane-1,2-diol, particularly ethane-1,2-diol.

Other particularly suitable are diols, in which the hydroxyl groups are separated by 3 carbon atoms, and, hence, form a very stable 6 membered ring in a ketal. Particularly suitable diols of this type are propane-1,3-diol, butane-1,3-diol, 2-methylpropane-1,3-diol, 2-methylbutane-1,3-diol, 2,2-dimethylpropane-1,3-diol, 1,2-dimethylpropane-1,3-diol, 3-methylpentane-2,4-diol and 2-(hydroxymethyl)-cyclohexanol.

Preferably primary alcohols are used as diols.

The reaction conditions and stoichiometry used for the ketal formation are known to the person skilled in the art.

It is more preferred that the compound of formula (II-C) is selected from the group consisting of

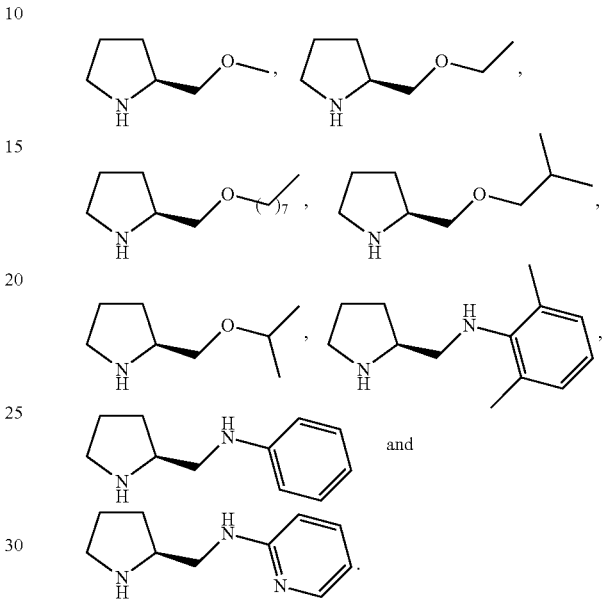

The pK$_a$ of the Brønsted acid having a pK$_a$ of between 5 and 10.5, can be measured at 25° C. in DMSO and is used in combination with compound of formula (II-C).

Suitable Brønsted acids are particularly those mentioned in table II in Bordwell, *Acc. Chem. Res.* 1988, 21, 456-463 having a pK$_a$ of between 5 and 10.5.

Preferred is that the Brønsted acid is selected from the group consisting of trifluormethane sulphonamide, p-nitrobenzoic acid, 3,5-dinitrobenzoic acid and 3,5-bis(trifluoromethyl)benzoic acid, more preferably from the group consisting of trifluormethane sulphonamide and p-nitrobenzoic acid.

Most preferred is the Brønsted acid either trifluormethane sulphonamide or p-nitrobenzoic acid.

It is preferred that the ratio of molar amounts of Brønsted acid to chiral compound of formula (II-C) is between 1:2 and 4:1, preferably in the range from 1:1 and 2:1. It is, furthermore, preferred that the ratio of Brønsted acid to chiral compound of formula (II-C) is selected so that slightly more than one acid proton from the Brønsted acid is available per NH group of the compound of formula (II-C).

In the second embodiment of the invention the reaction between compound of formula (II-A) and compound of formula (II-B) or a ketal thereof is done in the presence of at least one chiral compound of formula (II-C-A) having a pK$_a$ of between 5 and 10.5, measured at 25° C. in DMSO, or an internal salt thereof.

The substituent A in the formulae of this document represents a substituent carrying a Brønsted acid functional group. The substituent carrying a Brønsted acid functional group is particularly an alkylene group having 1 to 6 carbon atoms and optionally oxygen atoms in the alkylene chain, carrying a Brønsted acid functional group. Preferably such a substituent A is an alkylene group with 1 to 3 carbon atoms, most preferably a methylene group, carrying a Brønsted acid functional group.

It is preferred that the substituent A carries one Brønsted acid functional group.

The compound of formula (II-C-A) is most preferably the compound of formula (IV)

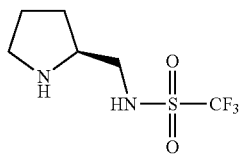

(IV)

The compounds of formula (II-C) and (II-C-A) are chiral compounds. The compounds are either used directly as pure stereoisomers or separated by known techniques into the R- and the S-stereoisomer prior to the use for the present invention.

It has been found that the isomer shown in formula (II-C), respectively (II-C-A), yields preferentially the isomers of compound of formula (I), respectively of formula (V), showing the R-configuration at the chiral centre indicated by *.

Therefore, it has been found that the chirality of the compound of formula (II-C) or of formula (II-C-A) has an important effect on the chirality of the compound being formed, i.e. on compound of formula (I) or of formula (V).

Hence, the isomer having the R-configuration at the chiral centre marked by * in formula (I) is preferentially formed in respect to the corresponding isomer having the S-configuration at said chiral centre by the above process.

On the other hand, it has been found that when using the stereoisomers shown in formula (II-C'), respectively (II-C-A'), instead of compounds of formula (II-C), respectively (II-C-A), preferentially the isomers of compound of formula (I) resp. formula (V) showing the S-configuration at the chiral centre indicated by * are obtained.

Compound of formula (II-A) and compound of formula (II-B) or a ketal thereof are reacted either in the presence of at least one chiral compound of formula (II-C) and of at least one Brønsted acid having a pK$_a$ of between 5 and 10.5, measured at 25° C. in DMSO or in the presence of at least one chiral compound of formula (II-C-A) having a pK$_a$ of between 5 and 10.5, measured at 25° C. in DMSO, or an internal salt thereof.

This reaction occurs in an organic solvent. In one embodiment the reaction is undertaken in an organic solvent which is a hydrocarbon, preferably in an aromatic hydrocarbon, particularly in toluene, particularly at a temperature of preferably between 80° C. and 150° C., more preferably of between 90° C. and 140° C., most preferably at a temperature of between 100 and 110° C. at ambient pressure. It is preferred that the reaction temperature is about 5 to 10° C. below the boiling point of the solvent.

In another embodiment the reaction is undertaken in an organic polar solvent which is selected from the group consisting of alcohols, ethers, esters, carbonitriles, halogenated hydrocarbons and lactams. Particularly suitable polar solvents are acetonitrile, ethyl acetate, methanol, ethanol, dichloromethane, tetrahydrofuran (THF), N-methylpyrrolidone (NMP), 1,2-dichloroethane, 2,2,2-trifluoroethanol and isopropanol. However, it has been observed that the water, being an inorganic polar solvent, is not suitable as solvent because no conversion was detected.

Furthermore, it has been shown that the amount of organic solvent is preferably chosen so that at least a 4% by weight solution of compound of formula (II-A) is obtained. In a preferred embodiment the weight ratio between compound of formula (II-A) and organic solvent is between 2:98 and 80:20, particularly between 3:97 and 50:50, preferably between 4:96 and 30:70.

It has been found that the lower the temperature for the reaction of compound of formula (II-A) and compound of formula (II-B) or a ketal thereof is, the higher the chiral purity of the compound of formula (I) resp. (V) in view of chirality at the chiral centre indicated by * is. This chiral purity is expressed by the enantiomeric excess (ee) being determined by the absolute value of the difference of amounts of the R and S isomers divided by the sum of amounts of both isomers: and is normally expressed in %.

$$ee = \text{abs}\left(\frac{[R] - [S]}{[R] + [S]}\right)$$

We have been able to show that by using a reaction temperature of 0° C. the process has yielded in the formation of a product having an enantiomeric excess up to 40%, corresponding to a ratio of [R]/[S] of 2.3. However, the reaction rate was rather low.

In view of reaction rate, it is preferred to have the reaction taking place at higher temperatures higher than 0° C.

Furthermore, it might be helpful, particularly in the case where at low reaction temperatures are used, to use molecular sieves in the reaction medium.

The enantiomeric ratio can be increased further by optimizing the reaction conditions. The larger the enantiomeric ratio is the better. However, also at lower enantiomeric ratios the invention can be advantageous as the complete separation of the isomers, such as by chromatography, particularly by chromatography using chiral stationary phases, needs much less efforts as compared to a racemic mixture. Hence, the enantiomeric ratio should be at least 15%, preferably at least 20%, more preferably at least 25%.

In a further aspect, the invention relates to a process of manufacturing a compound of formula (V) comprising the steps
i) process of manufacturing of formula (I) as it has been described in detail above;
ii) reducing of compound of formula (I)

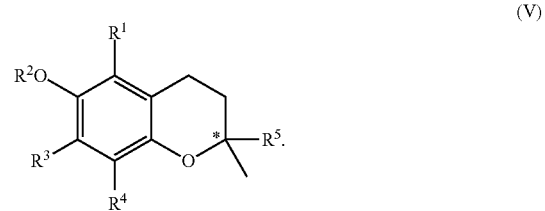

(V)

The substituents $R^1$, $R^2$, $R^3$, $R^4$ and $R^5$ are already discussed in detail above.

Most preferably the chiral isomers of formula (V) are the isomers selected from the group consisting of α-Tocopherol ($R^1=R^3=R^4=CH_3$, $R^5=$(II-A), particularly (II-ARR), $R^2=H$), β-Tocopherol ($R^1=R^4=CH_3$, $R^3=H$, $R^5=$(II-A), particularly (II-ARR), $R^2=H$), γ-Tocopherol ($R^1=H$, $R^3=R^4=CH_3$, $R^5=$(II-A), particularly (II-ARR), $R^2=H$), δ-Tocopherol ($R^1=R^3=H$, $R^4=CH_3$, $R^5=$(II-A), particularly (II-ARR), $R^2=H$), α-Tocotrienol ($R^1=R^3=R^4=CH_3$, $R^5=$(II-B), $R^2=H$),
β-Tocotrienol ($R^1=R^4=CH_3$, $R^3=H$, $R^5=$(II-B), $R^2=H$),
γ-Tocotrienol ($R^1=H$, $R^3=R^4=CH_3$, $R^5=$(II-B), $R^2=H$),
δ-Tocotrienol ($R^1=R^3=H$, $R^4=CH_3$, $R^5=$(II-B), $R^2=H$), and the esters, particularly the acetates ($R^2=COCH_3$), or phosphates thereof.

Particularly preferred compounds of formula (V) are esters of organic and inorganic acids. Examples of esters of organic acids are acetate and succinate esters, esters of inorganic esters are tocopheryl phosphates, ditocopheryl phosphates, particularly α-tocopheryl phosphate and α-ditocopheryl phosphate.

Most preferred compounds of formula (V) are tocopherols and tocopheryl acetates.

The reduction in step ii) can be made by different ways. Typically it is reduced by using a reduction means.

Preferably the reduction is made by metallic zinc in the presence of an acid or an acid mixture, for example as disclosed for in U.S. Pat. No. 6,096,907 or EP 0 989 126 the whole disclosure of which is incorporated herein by reference.

The reduction step ii) is typically done in stirred vessel under inert atmosphere. It is further preferred that the step ii) is done at a temperature in the range of 30 to 90° C., particularly between 40 and 65° C.

After completion of the reaction the compound of formula (V) is purified, particularly by means of extraction.

It has been observed that the reduction of compound of formula (I) to compound of formula (V) does not modify the chirality of the chiral centre indicated by * in the formulae (I) resp. (V).

It has been found that the isomer shown in formula (II-C), respectively (II-C-A), yields preferentially the isomers of compound of formula (I), respectively of formula (V), showing the R-configuration at the chiral centre indicated by *.

Hence, the isomer having the R-configuration at the chiral centre marked by * in formula (V) is preferentially formed in respect to the corresponding isomer having the S-configuration at said chiral centre.

On the other hand, it has been found that when using the stereoisomers shown in formula (II-C'), respectively (II-C-A'), instead of compounds of formula (II-C), respectively (II-C-A), preferentially the isomers of compound of formula (I) resp. formula (V) showing the S-configuration at the chiral centre indicated by * are obtained.

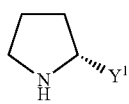

(II-C')

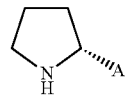

(II-C-A')

In a further aspect, the invention relates to a composition comprising a) at least one compound of formula (II-A) and b) at least one ketone of formula (II-B) or a ketal thereof and c) at least one organic solvent and either a mixture or reaction product of d) at least one chiral compound of formula (II-C) and e) at least one Brønsted acid having a $pK_a$ of between 5 and 10.5, measured at 25° C. in DMSO;

or e) at least one chiral compound of formula (II-C-A) having a $pK_a$ of between 5 and 10.5, measured at 25° C. in DMSO, or an internal salt thereof

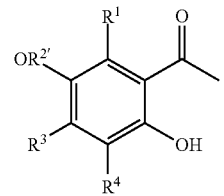

(II-A)

(II-B)

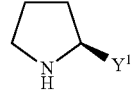

(II-C)

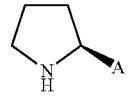

(II-C-A)

The substituents $R^1$, $R^{2'}$, $R^3$, $R^4$, $R^5$, $Y^1$ and A have already been discussed in detail above.

Furthermore, details for the compound of formula (II-A), for compound of formula (II-B) or a ketal thereof, for chiral compound of formula (II-C) and for chiral compound of formula (II-C-A) as well their preferred embodiments and their ratios have been discussed in detail already above.

As described above this composition is very suitable for the synthesis of compound of formula (I) which can be transformed to compound of formula (V).

As has been shown above in great detail, the present invention relates to the manufacturing of compounds of formula (I).

6-hydroxy-2,7,8-trimethyl-2-(4,8,12-trimethyltridecyl) chroman-4-one. As this compound, being represented by formula (VI), is not yet known, it represents a further aspect of the present invention.

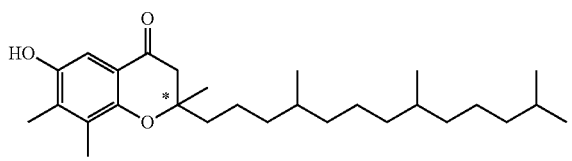 [SMILES: CC(C)=CCC/C(C)=C/CC/C(C)=C/CCC1(C)CC(=O)c2c(C)c(O)c(C)c(C)c2O1]

(VI)

It has been shown that compound of formula (VI) can be manufactured in a stereospecific matter in view of the 2-position in the chromanones ring and that it can be easily converted to γ-tocopherol.

Therefore, a chiral compound of formula (II-C) can be used for the preparation of tocopherols or tocotrienols as it also discussed in great detail above. This use particularly involves the use of of a chiral compound of formula (II-C) for the preparation of compound of formula (I) followed by transformation to compound of formula (V). When this use is made in the presence of at least one Brønsted acid having a $pK_a$ of between 5 and 10.5, measured at 25° C. in DMSO the formation of the stereoisomer of formula (I) resp. (V) having the R configuration at the chiral carbon centre marked by * in formula (I) resp. (V) is obtained in an excess related to the corresponding stereoisomer having the S-configuration.

The details for chiral compound of formula (II-C), for compound of formula (I), for formula (V) and for one Brønsted acid as well their preferred embodiments and their ratios have been discussed in detail already above.

Examples

The present invention is further illustrated by the following experiments.
Use of Different Acids
0.5 mmol of 2-acetyl-3,5,6-trimethylhydroquinone and 0.795 mmol of the acid indicated in table 1 have been suspended in a 20 mL round bottom flask equipped with a magnetic stirring bar, heating device, water separator and argon supply at 23° C. in 2.5 mL (23.5 mmol) toluene. Then 0.514 mmol of E,E-farnesylacetone has been is added and finally 0.795 mmol (S)-2-(methoxymethyl)-pyrrolidine. The reaction mixture has been stirred for the time at the temperature as indicated in table 1. While heating to 120° C. water is distilled off and the reaction mixture was getting brown. After the indicated time, the reaction mixture was cooled to 23° C. Then 1 mL of 2 N HCl has been added and the mixture has been transferred to a separation funnel and was well shaken. The toluene phase was separated and washed with portions of 10 mL water until a neutral water phase was obtained. The organic layers are dried over sodium sulfate, filtered and concentrated at 40° C. and 10 mbar.

The product formed and isolated by column chromatography on $SiO_2$ has been identified to be 6-hydroxy-2,5,7,8-tetramethyl-2-((3E,7E)-4,8,12-trimethyltrideca-3,7,11-trien-1-yl)chroman-4-one:

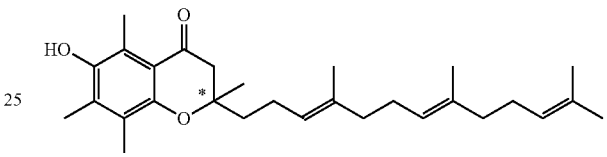

$^1$H NMR (CDCl$_3$, 300 MHz) δ 1.30 (s, 3H); 1.51 (s, 6H); 1.52 (s, 3H); 1.54-1.58 (m, 1H); 1.61 (d, J=0.9 Hz, 3H); 1.67-1.78 (m, 1H); 1.67-2.10 (m, 10H); 2.08 (s, 3H); 2.16 (s, 3H); 2.48 (s, 3H); 2.51 (d, J=15.8 Hz, 1H); 2.68 (d, J=15.8 Hz, 1H), 4.45 (s br, 1H); 4.99-5.05 (m, 3H) ppm.
$^{13}$C NMR (CDCl$_3$, 75.5 MHz) δ 12.1; 12.8; 13.3; 15.9; 16.0; 17.7; 22.2; 23.7; 25.1; 26.6; 26.8; 39.4; 39.7 (2C); 49.5; 79.4; 116.7; 120.4; 123.5; 124.0; 124.1; 124.4; 131.3; 132.0; 135.1; 135.7; 145.8; 152.8; 195.2 ppm.
Determination of enantiomeric ratio: HPLC, Chiralcel® OD-H, 250×4.6 mm, 10 mL EtOH, 990 mL n-hexane, 1.0 mL/min; detection at 220 nm.

TABLE 1

Different Brønsted acids.

| | Acid | pKa (in DMSO) | $t_{23°C.}$ | $t_{120°C.}$ | Yield[1] [%] | [R]:[S] | ee [%] |
|---|---|---|---|---|---|---|---|
| Ref. 1 | none | | 20 | 1.5 | 2.2 | 50:50 | 0 |
| Ref. 2 | trifluoromethanesulfonic acid | 1 | 20 | 1 | dec.[2] | — | 0 |
| Ref. 3 | (−)-camphorsulfonic acid | 1.6 | 20 | 2 | 4 | 50:50 | 0 |
| 1 | dichloroacetic acid | 6.4 | 17 | 24 | 8 | 59:41 | 18 |
| 2 | 3,5-dinitro-benzoic acid | 7.4 | 16 | 18 | 33 | 63:37 | 26 |
| 3 | 4-nitrobenzoic acid | 9.0 | 16 | 2 | 41 | 63:37 | 26 |
| 4 | 3,5-bis(trifluoromethyl)-benzoic acid | 9.1 | 16 | 2 | 34 | 63:37 | 26 |
| 5 | trifluoromethane-sulfonamide | 9.7 | 20 | 1 | 9 | 60:40 | 20 |
| Ref. 4 | benzoic acid | 11.0 | 20 | 1.5 | 28 | 52:48 | 4 |
| Ref. 5 | acetic acid | 12.3 | 20 | 1.5 | 2 | 52:48 | 4 |
| Ref. 6 | p-toluenesulfonamide | 16.1 | 20 | 1 | 12 | 50:50 | 0 |
| Ref. 7 | (1S)-10-camphor-sulfonamide | 17 | 20 | 2 | 2 | 50:50 | 0 |
| Ref. 8 | methanesulfonamide | 17.5 | 20 | 1 | 20 | 50:50 | 0 |

[1]yield relative to 2-acetyl-3,5,6-trimethylhydroquinone
[2]dec. = decomposition Use of Different Pyrrolidines 0.5 mmol of 2-acetyl-3,5,6-trimethylhydroquinone and 0.795 mmol of p-nitrobenzoic acid have been suspended in a 20 mL round bottom flask equipped with a magnetic stirring bar, heating device, water separator and argon supply at 23° C. in 2.5 mL toluene. Then 0.514 mmol of E,E-farnesylacetone is added and finally 0.795 mmol of the base indicated in table 2. The reaction mixture has been stirred for 16 h at 23° C. followed by 2 h at 120° C. While heating to 120° C. water is distilled off and the reaction mixture was getting brown. Then, the reaction mixture was cooled to 23° C. and 1 mL of 2 N HCl has been added and the mixture has been transferred to a separation funnel and was well shaken. The toluene phase was separated and washed with portions of 10 mL water until a neutral water phase was obtained. The organic layers are dried over sodium sulfate, filtered and concentrated at 40° C. and 10 mbar.

The product formed has been identified to be 6-hydroxy-2,5,7,8-tetra-methyl-2-((3E,7E)-4,8,12-trimethyltrideca-3,7,11-trien-1-yl)chroman-4-one (characterization see point "use of different acids").

TABLE 2

Different bases, particularly pyrrolidine derivatives.

| | Base | Yield[1] [%] | [R]:[S] | ee [%] |
|---|---|---|---|---|
| Ref. 9 | pyrrolidine | 59 | 50:50 | 0 |
| Ref. 10 | (S)-pyrrolidin-2-ylmethanamine | 33 | 50:50 | 0 |
| Ref. 11 | N-methylpyrrolidine | 0 | —[2] | —[2] |
| 6 | (S)-2,6-dimethyl-N-(pyrrolidin-2-ylmethyl)aniline | 17 | 63:37 | 26 |
| 7 | (S)-tert-butyl (pyrrolidin-2-ylmethyl)carbamate | 55.8 | 55:45 | 10 |
| 8 | (S)-pyrrolidin-2-ylmethanol | 4.1 | 58:42 | 16 |
| 9 | (S)-2-(ethoxymethyl)pyrrolidine | 59 | 64:36 | 28 |
| 10 | (S)-1-(pyrrolidin-2-ylmethyl)pyrrolidine | 28 | 55:45 | 10 |
| Ref. 12 | (2S,5S)-2,5-bis(methoxymethyl)pyrrolidine | 0 | —[2] | —[2] |
| Ref. 13 | (S)-2-(tert-butyl)-3-methylimidazolidin-4-one | 0 | —[2] | —[2] |
| Ref. 14 | (S)-diphenyl(pyrrolidin-2-yl)methanol | 0 | —[2] | —[2] |

[1]yield relative to 2-acetyl-3,5,6-trimethylhydroquinone
[2]as no reaction occurred (yield: 0%) no measurements were possible.

Use of Chiral Pyrrolidines Carrying a Brønsted Acid Functional Group 0.5 mmol of 2-acetyl-3,5,6-trimethylhydroquinone and 0.795 mmol of (S)-1,1,1-trifluoro-N-(pyrrolidin-2-ylmethyl)methanesulfonamide have been suspended in a 20 mL round bottom flask equipped with a magnetic stirring bar, heating device, water separator and argon supply at 23° C. in 2.5 mL toluene. Then 0.514 mmol of E,E-farnesylacetone is added. The reaction mixture has been stirred for 16 h at 23° C. followed by 2 h at 120° C. While heating to 120° C. water is distilled off and the reaction mixture was getting brown. Then, the reaction mixture was cooled to 23° C. and 1 mL of 2 N HCl has been added and the mixture has been transferred to a separation funnel and was well shaken. The toluene phase was separated and washed with portions of 10 mL water until a neutral water phase was obtained. The organic layers are dried over sodium sulfate, filtered and concentrated at 40° C. and 10 mbar.

The product formed has been identified to be 6-hydroxy-2,5,7,8-tetra-methyl-2-((3E,7E)-4,8,12-trimethyltrideca-3,7,11-trien-1-yl)chroman-4-one. The product was obtained in 58% yield and showed an enantiomeric ratio of 61:39 (corresponding to an ee of 22%).

Use of Different Substrates to be Condensed 0.5 mmol of compound of formula (II-A), having the groups $R^3=R^4=CH_3$ and $R^1$ and $R^{2'}$ as indicated in table 3, and 0.795 mmol of 3,5-dinitrobenzoic acid have been suspended in a 20 mL round bottom flask equipped with a magnetic stirring bar, heating device, water separator and argon supply at 23° C. in 2.5 mL toluene. Then 0.514 mmol of compound of formula (II-B), having the group $R^5$ as indicated in table 3, has been is added and finally 0.795 mmol (S)-2-(methoxymethyl)pyrrolidine. The reaction mixture has been stirred during 16 hours at 23° C. While heating to 120° C. water is distilled off and the reaction mixture was getting brown. After the indicated time, the reaction mixture was cooled to 23° C. Then 1 mL of 2 N HCl has been added and the mixture has been transferred to a separation funnel and was well shaken. The toluene phase was separated and washed with portions of 10 mL water until a neutral water phase was obtained. The organic layers are dried over sodium sulfate, filtered and concentrated at 40° C. and 10 mbar.

The identity of the product formed has been proven by NMR and the the ratio of [2R] to [2S] stereoisomers has been determined by HPLC: Chiralcel® OD-H, 250×4.6 mm, 10 mL EtOH, 990 mL n-hexane, 1.0 mL/min; detection at 220 nm.

TABLE 3

| | $R^{2'}$ | $R^1$ | $R^3$ | $R^4$ | $R^5$ | $t_{23°C.}$ [h] | $t_{120°C.}$ [h] | Yield [%] | [R]:[S] |
|---|---|---|---|---|---|---|---|---|---|
| 11 | C(O)CH$_3$ | CH$_3$ | CH$_3$ | CH$_3$ | C$_{16}$H$_{27}$[3] | 17 | 2 | 25[1] | 63:37 |
| 12 | C(O)CF$_3$ | CH$_3$ | CH$_3$ | CH$_3$ | C$_{16}$H$_{27}$[3] | 16 | 18 | 1[1] | 63:37 |
| 13 | H | CH$_3$ | CH$_3$ | CH$_3$ | C$_{16}$H$_{33}$[4] | 16 | 2 | 90[2] | 63:37 |
| 14 | H | H | H | H | C$_{16}$H$_{33}$[4] | 16 | 2 | 26[2] | 67:33 |

Different staring materials.
[1]yield: based on sum of the ester derivative plus the free phenol formed by partial hydrolysis of the ester during the reaction and work-up; relative to compound of formula (II-A);
[2]yield relative to compound of formula (II-A)
[3],[4]

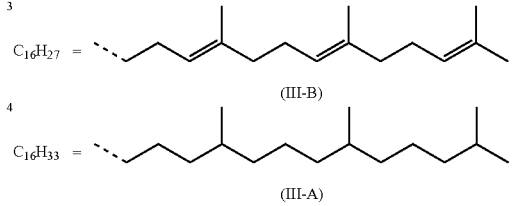

Synthesis of 6-hydroxy-2,7,8-trimethyl-2-(4,8,12-trimethyltridecyl)chroman-4-one (15) (Compound of Formula (VI)

2.5 mmol of 1-(2,5-dihydroxy-3,4-dimethylphenyl)ethanone and 4.0 mmol 4-nitrobenzoic acid were suspended in a 25 mL round bottom flask equipped with a magnetic stirring bar, heating device, water separator and argon supply at 23° C. in 12.5 mL toluene. To this brown suspension 2.58 mmol of E,E-farnesylacetone and afterwards 4.0 mmol (S)-2-(methoxymethyl)pyrrolidine were added. The temperature of the reaction mixture rose to 25° C., then stirring was continued for 17.5 h at 23° C. Then the mixture was heated to reflux (150° C. oil bath temperature, internal temp. 116° C.), and water was distilled off (the water separator was filled with toluene before). The reaction mixture was cooled to 23° C. Then 5 mL of 2 N HCl were added, the mixture stirred for 15 min, transferred to a separation funnel and well shaken. The toluene phase was separated and washed successively with four portions of 15 mL water each until a neutral water phase was obtained. The organic layer was dried over sodium sulfate, filtered, concentrated at 50° C. and 20 mbar, and dried at 23° C. and 0.02 mbar for 2 h.

The crude product (1.271 g black oil with solids) was purified by column chromatography (100 g silica gel 60, n-hexane/EtOAc 9:1). After evaporation (40° C. and 20 mbar) and drying at 24° C. and 0.022 mbar for 2 h 6-hydroxy-2,7,8-tri-methyl-2-(4,8,12-trimethyltridecyl)chroman-4-one (15) was obtained (0.672 g black oil, purity 91.7 wt % by NMR, 97.1 area % by GC, yield 57%).

$^1$H NMR (CDCl$_3$, 300 MHz) δ 0.80-0.90 (m, 4 CH$_3$); 0.98-1.83 (m, 21 aliph. H); 1.37 (s, CH$_3$); 2.16 (s, 1 arom. CH$_3$); 2.22 (s, 1 arom. CH$_3$); 2.590 and 2.596 (d, J=16.5 and 16.6 Hz, 1H); 2.72 (d, J=16.7 Hz, 1H), 4.88 (s, OH); 7.12 (s, 1H$_{arom}$) ppm.

$^{13}$C NMR (CDCl$_3$, 75.5 MHz) δ 11.9; 13.0; 19.52; 19.58; 19.67; 19.73; 21.0; 22.62; 22.71; 23.88; 23.90; 24.4; 24.8; 28.0; 32.6; 32.8; 37.08; 37.17; 37.22; 37.28; 37.38; 37.43; 39.4; 39.54; 39.64; 47.60; 47.64; 80.6; 107.2; 117.6; 127.3; 128.2; 129.0; 133.9; 147.7; 152.4; 193.6 ppm.

MS (trimethylsilyl derivative): m/e=502 (M$^+$), 487 ([M-15]$^+$), 277 (100%), 237.

Determination of the ratio of [2R]-stereoisomers to [2S]-stereoisomers: HPLC, Chiralpak® IC, 250×4.6 mm, 10 mL EtOH, 990 mL n-hexane, 1.0 mL/min; detection at 220 nm; [2R]:[2S]=57:43.

Use of Different Solvents 0.5 mmol of 2-acetyl-3,5,6-trimethylhydroquinone and 0.795 mmol of p-nitrobenzoic acid have been suspended in a 20 mL round bottom flask equipped with a magnetic stirring bar, heating device, 4 Å molecular sieve and argon supply at 23° C. in 2.5 mL of the solvent indicated in table 4. Then 0.514 mmol of E,E-farnesylacetone has been added and finally 0.795 mmol (S)-2-(methoxymethyl)pyrrolidine. The reaction mixture has been stirred for 24 h at 40° C. Then the reaction mixture was cooled to 23° C. Then 1 mL of 2 N HCl has been added and the mixture has been transferred to a separation funnel and was well shaken. The toluene phase was separated and washed with portions of 10 mL water until a neutral water phase was obtained. The organic layers are dried over sodium sulfate, filtered and concentrated at 40° C. and 10 mbar.

The product formed has been identified to be 6-hydroxy-2,5,7,8-tetra-methyl-2-((3E,7E)-4,8,12-trimethyltrideca-3,7,11-trien-1-yl)chroman-4-one (characterization see point "use of different acids").

TABLE 4

Different solvents.

| | Solvent | Yield[1] [%] | [R]:[S] | ee [%] |
|---|---|---|---|---|
| 16 | ethyl acetate | 14 | 63:37 | 26 |
| 17 | isopropanol | 19 | 60:40 | 20 |
| 18 | 2,2,2-trifluoroethanol | 1 | 67:33 | 34 |
| 19 | 1,2-dichloroethane | 7 | 65:35 | 30 |
| 20 | N-methylpyrrolidone | 16 | 63:37 | 26 |
| 21 | propylene carbonate | 10 | 67:33 | 34 |
| Ref. 15 | water | 0 | —[2] | —[2] |

[1] yield relative to 2-acetyl-3,5,6-trimethylhydroquinone
[2] as no reaction occurred (yield: 0%) no measurements were possible.

Conversion of Chromanones to Chromans 6-hydroxy-2,5,7,8-tetramethyl-2-((3E,7E)-4,8,12-trimethyltrideca-3,7,11-trien-1-yl)chroman-4-one been transformed to α-tocotrienol by treatment with zinc dust and aqueous hydrochloric acid, as described in detail by Baldenius et al., EP 0 989 126 A1:

6-Hydroxy-2,5,7,8-tetramethyl-2-((3E,7E)-4,8,12-trimethyltrideca-3,7,11-trien-1-yl)chroman-4-one (5.0 mmol) (example 2) was dissolved under an argon atmosphere in 25 mL toluene, and 25% aqueous HCl (41.7 mL, 340 mmol) was added. To this mechanically stirred two-phasic mixture zinc dust (65 mmol) was added in small portions (ca. 0.5 g) during 4 h. Stirring was continued at 40° C. for 16 h and at 65° C. for 1 h. After completion of the reaction (TLC control), the mixture was cooled to room temperature and filtered through a pad of Dicalite. The filter residue was washed with 100 mL n-heptane, and the combined filtrates washed with 50 mL water. The organic layer was dried over sodium sulfate, filtered, concentrated at 40° C. and 10 mbar and dried for 2 h at 0.003 mbar at 23° C. The 2.22 g yellowish-brown oil was purified by column chromatography (100 g SiO$_2$ silica gel 60, n-hexane/EtOAc 9:1). After evaporation (40° C./20 mbar) and drying (0.021 mbar/23° C.) α-tocotrienol was obtained as a yellowish-brown oil (1.291 g, purity 93.9 wt %, yield 57%).

The compound obtained showed identical retention time in comparison to an authentic sample of natural (R,E,E)-α-tocotrienol, and the values obtained by measuring the $^1$H NMR (CDCl$_3$, 300 MHz) were identical with the values for α-tocotrienol, as for example reported by P. Schudel et al., Helv. Chim. Acta 1963, 46, 2517-2526.

Determination of enantiomeric ratio: HPLC, Chiralcel® OD-H, 250×4.6 mm, 0.5% EtOH in n-hexane, 1.0 mL/min; detection at 220 nm.

In analogy to the example given above, hexahydrofarnesylacetone (6,10,14-trimethylpentadecane-2-one) (example 15) has been transformed to γ-tocopherol by treatment with zinc dust and aqueous hydrochloric acid, as described by Baldenius et al., EP 0 989 126 A1. The compound obtained showed identical retention time in comparison to an authentic sample of γ-tocopherol, and the values obtained by measuring the $^1$H NMR (CDCl$_3$, 300 MHz) were identical with the values for γ-tocopherol, as for example reported by J. K. Baker and C. W. Myers, Pharmaceutical Research 1991, 8, 763-770.

In analogy to the example given above, 6-hydroxy-2,5,7,8-tetramethyl-2-(4,8,12-trimethyltridecyl)chroman-4-one (example 13) has been transformed to α-tocopherol by treatment with zinc dust and aqueous hydrochloric acid, as described by Baldenius et al., EP 0 989 126 A1. The compound obtained showed identical retention time in comparison to an authentic sample of α-tocopherol, and the values obtained by measuring the $^1$H NMR (CDCl$_3$, 300 MHz) were identical with the values for α-tocopherol, as for example reported by J. K. Baker and C. W. Myers, Pharmaceutical Research 1991, 8, 763-770.

The invention claimed is:

1. A process for manufacturing a compound of formula (I):

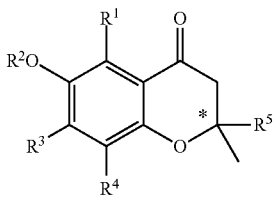

(I)

comprising the step of reacting a compound of formula (II-A) and a compound of formula (II-B) or a ketal thereof in the presence of an organic solvent and in the presence of either:
 (i) at least one chiral compound of formula (II-C) and of at least one Brønsted acid having a $pK_a$ of between 5 and 10.5, measured at 25° C. in DMSO, which is selected from the group consisting of trifluormethane sulphonamide, p-nitrobenzoic acid, 3,5-dinitrobenzoic acid and 3,5-bis(trifluoromethyl)benzoic acid; or
 (ii) at least one chiral compound of formula (II-C-A) having a $pK_a$ of between 5 and 10.5, measured at 25° C. in DMSO, or an internal salt thereof:

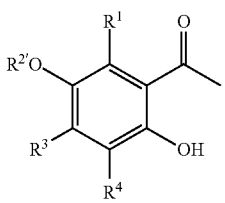

(II-A)

(II-B)

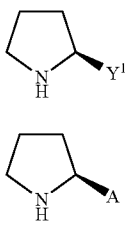

(II-C)

(II-C-A)

wherein
$R^1$, $R^3$ and $R^4$ are independently from each other hydrogen or methyl groups;
$R^2$ and $R^{2'}$ represents hydrogen or a phenol protection group;
$R^5$ represents either a linear or branched completely saturated $C_{6-25}$-alkyl group or a linear or branched $C_{6-25}$-alkyl group comprising at least one carbon-carbon double bond;

$Y^1$ represents either $CH_2Y^2$ or

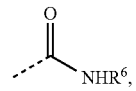

wherein
$R^6$ represents a linear or branched $C_{1-12}$-alkyl group which optionally further comprises at least one aromatic group and/or C=O and/or NH and/or $NH_2$ group;
$Y^2$ represents either OH or $OR^7$ or $NHR^7$ or $NHCOOR^7$ or

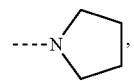

wherein
$R^7$ represents either:
 a linear or branched $C_{1-12}$-alkyl group which optionally further comprises at least one aromatic group and/or C=O and/or NH and/or $NH_2$ group; or
 an aryl group or a substituted aryl group or a heteroaryl group or a substituted heteroaryl group, and
A represents a substituent carrying a Brønsted acid functional group, and wherein
the dotted line(s) represents the bond(s) by which the corresponding substituent is bound to the rest of formula (II-C);
and wherein * represents the chiral centre of the chiral isomer of formula (I).

2. The process according to claim 1, wherein $R^5$ is of formula (III):

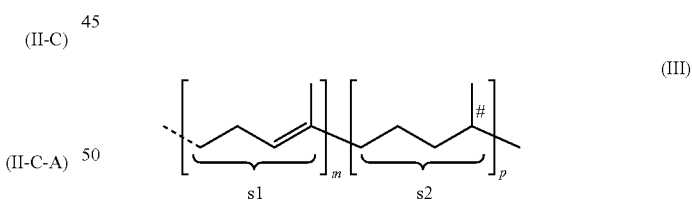

(III)

wherein m and p stand independently from each other for a value of 0 to 5 provided that the sum of m and p is 1 to 5,
and where the substructures in formula (III) represented by s1 and s2 can be in any sequence;
and the dotted line represents the bond by which the substituent of formula (III) is bound to the rest of the compound of formula (II-B) or formula (I);
and wherein # represents a chiral centre, obviously except in case where said centre is linked to two methyl groups.

3. The process according to claim 1, wherein $R^1 = R^3 = R^4 = CH_3$ or $R^1 = R^4 = CH_3, R^3 = H$ or $R^1 = H, R^3 = R^4 = CH_3$ or $R^1 = R^3 = H, R^4 = CH_3$.

4. The process according to claim 1, wherein the compound of formula (II-C) is selected from the group consisting of:

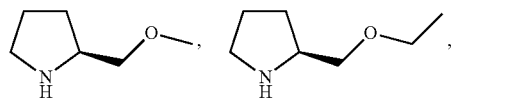

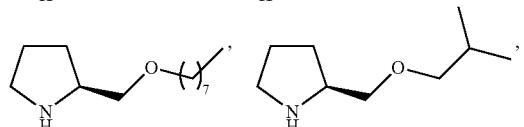

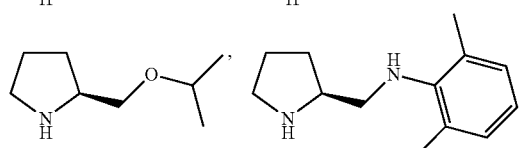

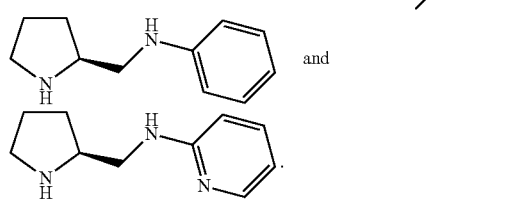

and

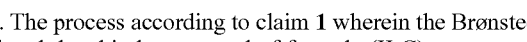

5. The process according to claim 1 wherein the Brønsted acid and the chiral compound of formula (II-C) are present in a molar ratio of the Brønsted acid to the chiral compound of formula (II-C) of between 1:2 and 4:1.

6. The process according to claim 1 wherein the compound of formula (II-C-A) is the compound of formula (IV):

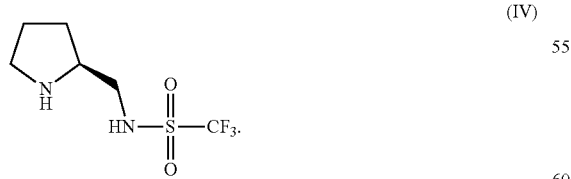

(IV)

7. A process for manufacturing a compound of formula (V) comprising the steps of:
i) manufacturing the compound of formula (I) according to claim 1; and
ii) reducing the compound of formula (I) to obtain the compound of formula (V):

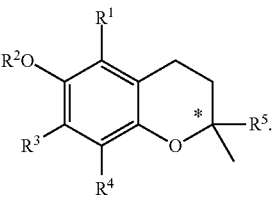

(V)

8. The process according to claim 1, wherein more of an isomer having the R-configuration at the chiral centre marked by * in formula (I) is formed as compared to a corresponding isomer having the S-configuration at said chiral centre.

9. A composition comprising:
a) at least one compound of formula (II-A) and
b) at least one ketone of formula (II-B) or a ketal thereof and
c) at least one organic solvent and either:
a mixture or reaction product of:
d) at least one chiral compound of formula (II-C) and
e) at least one Brønsted acid having a $pK_a$ of between 5 and 10.5, measured at 25° C. in DMSO, which is selected from the group consisting of trifluormethane sulphonamide, p-nitrobenzoic acid, 3,5-dinitrobenzoic acid and 3,5-bis(trifluoromethyl)benzoic acid;
or
f) at least one chiral compound of formula (II-C-A) having a $pK_a$ of between 5 and 10.5, measured at 25° C. in DMSO, or an internal salt thereof:

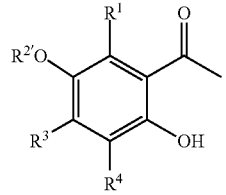

(II-A)

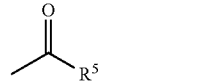

(II-B)

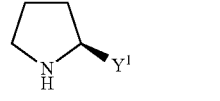

(II-C)

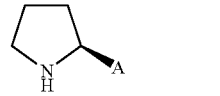

(II-C-A)

wherein $R^1$, $R^3$ and $R^4$ are independently from each other hydrogen or methyl groups;

$R^{2'}$ represents hydrogen or a phenol protection group;

$R^5$ represents either a linear or branched completely saturated $C_{6-25}$-alkyl group or a linear or branched $C_{6-25}$-alkyl group comprising at least one carbon-carbon double bond;

$Y^1$ represents either $CH_2Y^2$

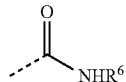

wherein $R^6$ represents a linear or branched $C_{1-12}$-alkyl group which optionally further comprises at least one aromatic group and/or C=O and/or NH and/or $NH_2$ group;

$Y^2$ represents either OH or $OR^7$ or $NHR^7$ or $NHCOOR^7$ or

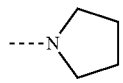

wherein $R^7$ represents either a linear or branched $C_{1-12}$-alkyl group which optionally further comprises at least one aromatic group and/or C=O and/or NH and/or $NH_2$ group or an aryl group or a substituted aryl group or a heteroaryl group or a substituted heteroaryl group, and A represents a substituent carrying a Brønsted acid functional group, and the dotted line(s) represents the bond(s) by which the corresponding substituent is bound to the rest of formula (II-C).

10. The composition according to claim 9, wherein $R^5$ is of formula (III):

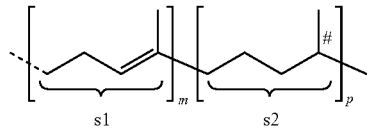

(III)

wherein m and p stand independently from each other for a value of 0 to 5 provided that the sum of m and p is 1 to 5, and where the substructures in formula (III) represented by s1 and s2 can be in any sequence;

and the dotted line represents the bond by which the substituent of formula (III) is bound to the rest of compound of formula (II-B);

and wherein # represents a chiral centre, obviously except in case where said centre is linked to two methyl groups.

11. The composition according to claim 9, wherein the compound of formula (II-C) is selected from the group consisting of:

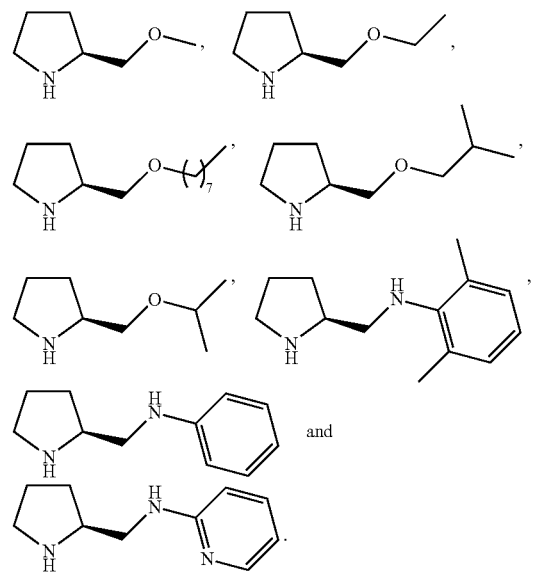

12. The composition according to claim 9 wherein the Brønsted acid and the chiral compound of formula (II-C) are present in a molar ratio of the Brønsted acid to the chiral compound of formula (II-C) of between 1:2 and 4:1.

* * * * *